(12) United States Patent
Qiu et al.

(10) Patent No.: US 7,122,377 B2
(45) Date of Patent: *Oct. 17, 2006

(54) ACID-LABILE ISOTOPE-CODED EXTRACTANT (ALICE) AND ITS USE IN QUANTITATIVE MASS SPECTROMETRIC ANALYSIS OF PROTEIN MIXTURES

(75) Inventors: Yongchang Qiu, Arlington, MA (US); Jack H. Wang, Lexington, MA (US); Rodney M. Hewick, Boston, MA (US)

(73) Assignee: Genetics Institute, LLC, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/919,365

(22) Filed: Aug. 17, 2004

(65) Prior Publication Data

US 2005/0014278 A1    Jan. 20, 2005

Related U.S. Application Data

(63) Continuation of application No. 10/045,170, filed on Oct. 22, 2001, now Pat. No. 6,902,936.

(60) Provisional application No. 60/242,643, filed on Oct. 23, 2000.

(51) Int. Cl.
    *G01N 33/00* (2006.01)
(52) U.S. Cl. .............. 436/86; 436/8; 436/15; 436/56; 422/61
(58) Field of Classification Search ............ 436/86, 436/161, 173, 174, 175, 8, 15, 56, 57; 422/61
    See application file for complete search history.

(56) References Cited

U.S. PATENT DOCUMENTS

| | | | |
|---|---|---|---|
| 4,847,325 A | 7/1989 | Shadle et al. | |
| 4,977,320 A | 12/1990 | Chowdhury | |
| 5,245,186 A | 9/1993 | Chait | |
| 5,288,644 A | 2/1994 | Beavis | |
| 5,306,562 A | 4/1994 | Barany | |
| 5,453,247 A | 9/1995 | Beavis | |
| 5,643,798 A | 7/1997 | Beavis | |
| 5,792,664 A | 8/1998 | Chait | |
| 6,602,498 B1 | 8/2003 | Shen | |
| 6,902,936 B1 * | 6/2005 | Qiu et al. | 436/86 |
| 6,905,879 B1 * | 6/2005 | Qiu et al. | 436/86 |
| 2003/0054570 A1 | 3/2003 | Qiu et al. | |

FOREIGN PATENT DOCUMENTS

| | | |
|---|---|---|
| EP | 1059531 | 12/2000 |
| WO | WO 91/04781 | 4/1991 |
| WO | WO 93/24834 | 12/1993 |
| WO | WO 00/11208 | 3/2000 |

OTHER PUBLICATIONS

Kalef, et al., "Arsenical-Based Affinity Chromatography of Vicinal Dithiol-Containing Proteins: Purification of L1210 Leukemia Cytoplasmic Proteins and the Recombinant Rat c-erb Aβ T3 Receptor", Analytical Biochemistry, vol. 212, No. 2, pp. 325-334, 1993, no month.
Krause, et al., "The Dominance of Arginine-Containing Peptides in MALDI-Derived Tryptic Mass Fingerprints of Proteins", Analytical Chemistry, vol. 71, No. 19, pp. 4160-4165, 1999, no month.
Mann, "Quantitative Proteomics?", Nature Biotechnology, vol. 17, pp. 954-955, 1999, no month.
Huang, et al., Bioconjugate Chemistry, vol. 9, pp. 612-617, 1998, no month.
Sechi, et al., "Modification of Cysteine Residues by Alkylation. A Tool in Peptide Mapping and Protein Identification", Analytical Chemistry, vol. 70, No. 24, pp. 5150-5158, 1998, no month.
Gygi, et al., "Quantitative Analysis of Complex Protein Mixtures Using Isotope-Coded Affinity Tags", Nature Biotechnology, vol. 17, pp. 994-999, 1999.
Fenyo, et al., "Protein Identification Using Mass Spectrometric Information", Electrophoresis, vol. 19, pp. 998-1005, 1998.

* cited by examiner

*Primary Examiner*—Maureen M. Wallenhorst
(74) *Attorney, Agent, or Firm*—Merchant & Gould, P.C.; Steven B. Kelber

(57) ABSTRACT

The method of the invention provides novel compounds, termed acid-labile isotope-coded extractants (ALICE), for quantitative mass spectrometric analysis of protein mixtures. The compounds contain a thiol-reactive group that is used to capture cysteine-containing peptides from all peptide mixtures, an acid-labile linker, and a non-biological polymer. One of the two acid-labile linkers is isotopically labeled and therefore enables the direct quantitation of peptides/proteins through mass spectrometric analysis. Because no functional proteins are required to capture peptides, a higher percentage of organic solvent can be used to solubilize the peptides, particularly hydrophobic peptides, through the binding, washing and eluting steps, thus permitting much better recover of peptides. Moreover, since the peptides are covalently linked to the non-biological polymer (ALICE), more stringent washing is allowed in order to completely remove non-specifically bound species. Finally, peptides captured by ALICE are readily eluted from the polymer support under mild acidic condition with high yield and permit the direct down stream mass spectrometric analysis without any further sample manipulation. In combination with our novel dual column two dimensional liquid chromatography-mass spectrometry (2D-LC-MS/MS) design, the ALICE procedure proves to a general approach for quantitative mass spectrometric analysis of protein mixtures with better dynamic range and sensitivity.

16 Claims, 1 Drawing Sheet

ACID-LABILE ISOTOPE-CODED EXTRACTANT (ALICE) AND ITS USE IN QUANTITATIVE MASS SPECTROMETRIC ANALYSIS OF PROTEIN MIXTURES

CROSS-REFERENCE TO RELATED APPLICATIONS

This application is a continuation of U.S. application Ser. No. 10/045,170, filed Oct. 22, 2001, now U.S. Pat. No. 6,902,936 issued on Jun. 7, 2005, which claims the benefit of the priority of U.S. Provisional Patent Application No. 60/242,643, filed Oct. 23, 2000.

BACKGROUND OF THE INVENTION

The present invention relates to the field of high-throughput quantitative protein analysis and, more specifically, to novel reagents for use in such analysis.

Most approaches to quantitative protein analysis are accomplished by combining protein separation, most commonly by high-resolution two-dimensional polyacrylamide gel electrophoresis (2D-PAGE), with mass spectrometry (MS)-based sequence or tandem mass spectrometry (MS/MS)-based sequence identification of selected, separated protein species.

S. P. Gygi, et al., *Nature Biotech*, 17:994–999 (October 1999) describes an approach to quantitative protein analysis based on a class of reagents termed isotope-coded affinity tags (ICAT), which consist of three functional elements: a specific chemical reactivity, an isotopically coded linker, and an affinity tag. The reagents described by Gygi utilize biotin as the affinity tag and rely upon biotin-avidin affinity binding to isolate the cysteine-containing peptides from the complex peptide mixture.

Although the ICAT approach has many advantages over the traditional 2D-PAGE/MS approaches, it does possess some intrinsic limitations. For example, ICAT adds a relatively large chemical moiety onto the cysteine-containing peptides and this functionality is very labile under collision induced dissociation (CID) condition and thus complicates the downstream data analysis. Non-specific binding is also a concern since the enrichment relies on non-covalent affinity binding between a protein (avidin) and the biotinylated peptides. Finally, the captured peptides are not readily eluted from the avidin beads with high recovery using MS-compatible conditions. Thus, there is a need in the art for additional reagents and methods for improving performance in quantitative mass spectrometric analysis of protein mixtures.

SUMMARY OF THE INVENTION

The invention provides polymer-based compounds useful for quantitative analysis of mixtures containing proteins. Advantageously, the compounds of the invention bind covalently with the peptides which they are used to tag, permitting the tagged peptides to be subjected to more rigorous washing techniques. Thus, the tagged peptides are more readily purified, without nonspecifically bound species. This results in lower background on MS spectra and thus provides an increase of dynamic range and sensitivity in quantitation and identification of the proteins.

In one aspect, the invention provides a method for the quantitative analysis of mixtures containing proteins. The method involves (a) reducing the disulfide bonds in the proteins of a sample to provide free thiol groups in cysteine-containing proteins; (b) blocking free thiols on the reduced proteins with a blocking reagent; (c) digesting the proteins in the sample using an enzyme such as trypsin; (d) reducing the peptides following the digestion step; (e) reacting cysteine-containing peptides with a reagent, wherein the reagent comprises a thiol-specific reactive group covalently bound to a polymer tag via a linker, wherein the linker can be differentially labeled with stable isotopes (optionally prior to or following any of the reduction steps); (f) washing the polymer-bound peptides to remove non-covalently bound compounds; (g) eluting the cysteine-containing peptides; and (h) subjecting the retrieved peptides to quantitative mass spectrometry (MS) analysis. In one embodiment, the method further involves performing steps (a) to (d) on a second sample; reacting cysteine-containing peptides in the second sample with a stable isotope-labeled form of the reagent, wherein in reacting step (e), the reagent used is a non-isotope labeled form of the reagent; mixing the peptides of the reacted sample following step (e) and the reacted second sample; and performing steps (g) and (h) on the peptides in the mixture.

In another aspect, the invention provides a compound useful for capturing cysteine-containing peptides. This compound is composed of a thiol-specific reactive group attached to a non-biological polymer via a linker. In one desirable embodiment, the reagent has the formula: A1—Linker—A2—polymer, wherein A1 is a thiol-reactive group and A2 is an acid labile group to which the polymer is attached.

In yet another aspect, the invention provides a reagent kit for the mass spectral analysis of proteins that comprises a compound of the invention.

Other aspects and advantages of the present invention are described further in the following detailed description of the preferred embodiments thereof

DETAILED DESCRIPTION OF THE INVENTION

Figure 1A:
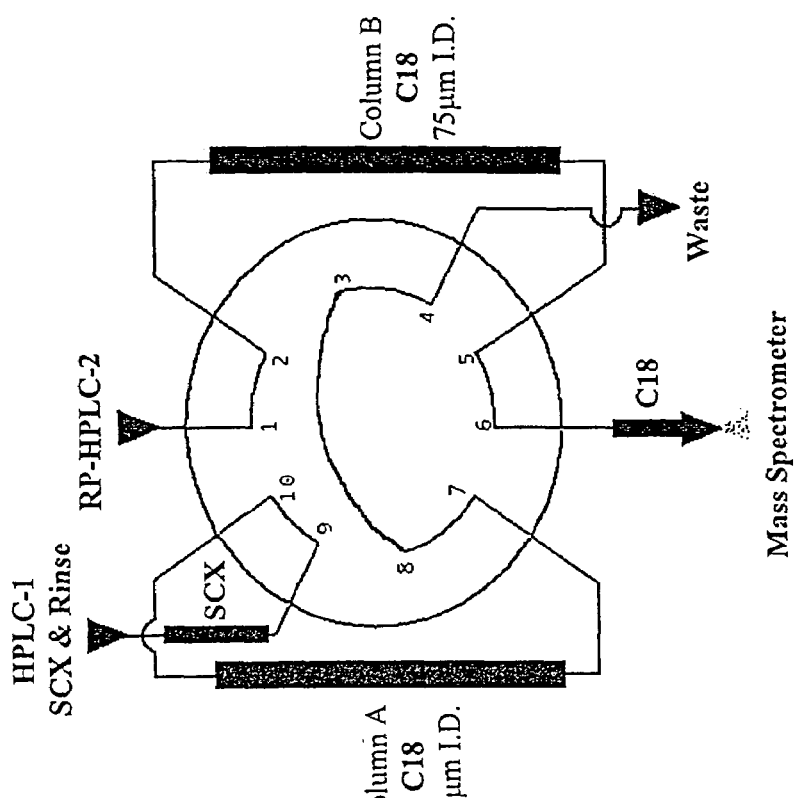
FIG. 1A and FIG. 1B provides a schematic of the automated 2D-LC/MS System of the invention.

The present invention provides a novel approach for the quantitative analysis of proteins using acid-labile isotope coded extractants (ALICE) which are useful for capturing cysteine-containing peptides. The advantage of this approach over the prior art, is that it replaces biotin-avidin affinity binding with acid-labile covalent binding to retrieve cysteine-containing peptides from the mixture. Since the binding is covalent, more stringent detergents or organic solvents can be used during the procedure to keep hydrophobic proteins and peptides in the solution and thus maximize the overall peptide recovery. Furthermore, the compounds and method of the invention avoid nonspecific peptide-protein binding. Removal of all detectable non-covalently bound species during the washing step(s) is also accomplished. Thus, the final cysteine-containing peptide solution is much less contaminated, resulting in higher sensitivity and dynamic range of MS analysis. Lastly, since the ALICE label is small in size and does not undergo fragmentation during MS/MS analysis, it does not interfere with the downstream MS analysis and database searching.

In one embodiment, the present invention provides a compound of the formula: A1—Linker—A2—polymer, wherein A1 is a thiol-reactive group and A2 is an acid labile group to which the polymer is attached. Alternatively the acid labile group may be absent and the polymer may be attached directly to the linker.

Most preferably, the polymer is a non-biological polymer. As used herein a non-biological polymer includes inorganic polymers and organic polymers which form a covalent bond with the acid-labile group, where present, or the linker. Suitably, an organic polymer selected does not interfere with the process steps in the method of the invention, e.g., is stable under basic conditions and in the presence of the detergents and/or organic solvents required to maintain the mixture in solution. In one suitable embodiment, the polymer used in the invention is a solid substrate composed of a homopolymer or a heteropolymer containing polystyrene, polyethylene, polyacrylamide, polyacrylein, polyethylene glycol, or the like. Suitable polymers and solid substrates, e.g., resins, beads or the like, are available from a variety of commercial sources including Sigma-Aldrich, NovaBiochem, and Beckman-Coulter, or may be synthesized using known techniques. An example of one suitable synthesis technique is provided in Example 1 below. However, the invention is not so limited.

In one embodiment, the polymer is covalently bound to the linker via an acid-labile group that provides the compound of the invention with the ability to be readily eluted using an acidic reagent. In one preferred embodiment, the acid-labile group bound to the polymer has the following stricture:

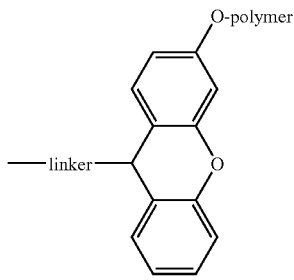

in which the linker is —CONH—, —COO—, or another amide or ester. However, other structures can be readily synthesized to contain other suitable groups that provide similar qualities to the compound in terms of stability and accessibility to acid elution. Examples of suitable acid-labile groups include:

Rink Amide Linker:

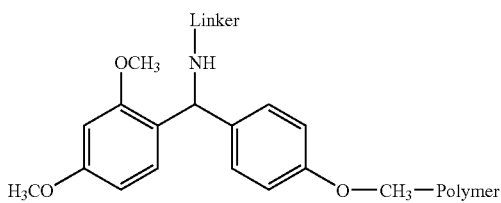

DHP Linker:

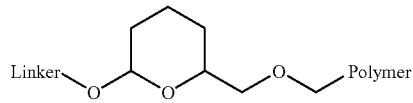

Siber Linker:

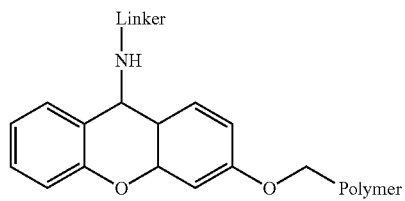

Trityl Linker:

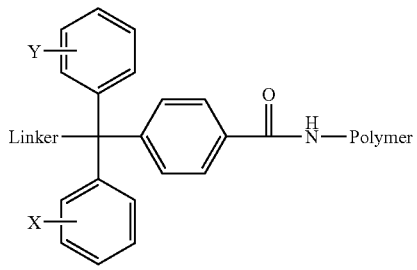

Wang Linker:

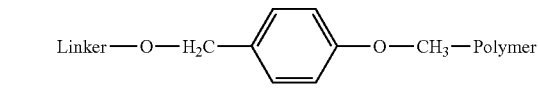

In certain embodiments, this function may be provided by the linker, and the acid labile group may be absent.

The linker is any structure that may be differentially labeled with stable isotopes for use in MS techniques. In one embodiment, the linker contain from 1 to 100 atoms in length, about 3 to about 50 atoms in length, or about 5 to about 15 atoms in length, which are composed of carbon, and optionally, one or two atoms selected from O, S, NH, NR, NR', CO, C(O)O, C(O)S, S—S, SO$_2$, C(O)—NR', CS—NR', or Si—O. Optionally, one or more of the C atoms may be substituted with a small alkyl ($C_1$–$C_6$), alkenyl, alkoxy, aryl, or diaryl groups. For example, the linker may be an alkyl, alkenyl, or alkynyl group, optionally substituted as described above. In another example, the linker may itself contain one or more O, S, NH, NR, NR', CO, C(O)O, C(O)S, S—S, SO$_2$, C(O)—NR', CS—NR', Si—O groups bound to one or more C atoms, which may be optionally substituted.

In one embodiment, the linker is a structure (e.g., an alkyl group) which contains a substitution of about four to about twelve atoms with a stable isotope. However, in certain embodiments, it is desirable for the linker to contain substitutions of at least six atoms with a stable isotope. For example, for peptides at the higher end of the molecular weight range at which MS is useful (e.g., about 2000 Da to 3500 Da) it may be desirable for the linker to contain eight, ten, twelve or more substitutions, in order to achieve the differential analysis required; whereas peptides at the lower end of the molecular weight range for MS (e.g., about 500 to 2000 Da) may require only four to six substitutions. For the selected number of substitutions, any one or more of the hydrogen, nitrogen, oxygen, carbon, or sulfur atoms in the linker may be replaced with their isotopically stable isotopes: $^2H$, $^{13}C$, $^{15}N$, $^{17}O$, $^{18}O$, or $^{34}S$.

Thus, the linker group has a structure that accommodates the number of isotope substitutions desired. The selection of this structure is not a limitation of the present invention. One or more of the atoms in the linker can be substituted with a stable isotope to generate one or more substantially chemically identical, but isotopically distinguishable compounds. Additionally or alternatively, the linker also optionally provides desired acid labile properties to the compound.

The compound of the invention further contains a functional group that is reactive, preferably specifically, with cysteine residues. Desirably, the reactive group is selected from the group consisting of either maleimide (see below)

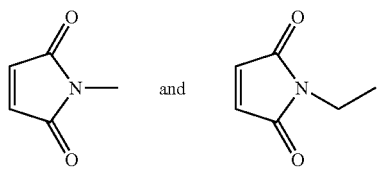

or α-haloacetyl groups such as X—CH$_2$CO—. Most suitably, the X is selected from halogens such as iodine, bromine, and chorine to form iodoacetyl, bromoacetyl, or chloroacetyl functionalities.

In another alternative, the thiol-reactive group may be selected from other α-, β-conjugated double bond structures, such as

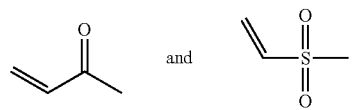

and the like. Still other reactive group can readily be synthesized to contain other thiol-specific reactive groups for use in binding cysteine-containing peptides.

In one preferred embodiment, a compound of the invention has the formula:

Light ALICE

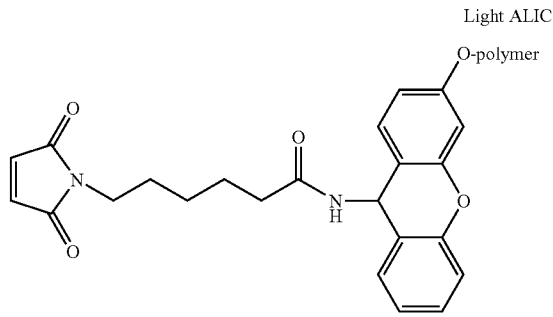

In one desirable embodiment, this compound is isotopically modified as follows.

Heavy ALICE

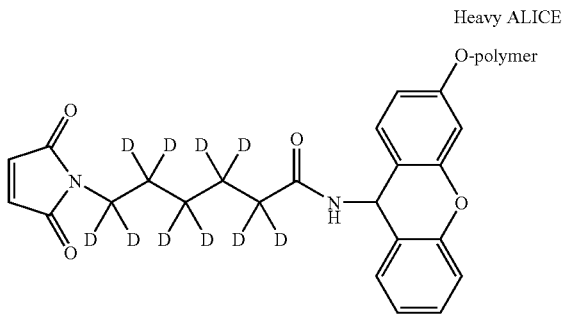

However, the invention is not so limited. One of skill in the art can readily provide light ALICE with other stable isotopes. Further, one of skill in the art can readily produce other suitable compounds in view of the guidance provided herein.

Method of Using the Compounds of the Invention

The compounds of the invention are particularly useful in mass spectrometric methods for quantitation and identification of one or more proteins in a mixture. The peptides analyzed by the method of the invention are most preferably about 500 Daltons (Da) to about 3500 Da in size, but may be larger. Suitably, these peptides are formed upon enzymatic digestion of proteins in a complex mixture. The protein mixture may be a sample from a cell or tissue culture, or biological fluids, cells or tissues. Samples from a culture include cell homogenates and cell fractions. Biological fluids include urine, blood (including, e.g., whole blood, plasma and sera), cerebrospinal fluid, tears, feces, saliva, and lavage fluids. The mixtures may include proteins, lipids, carbohydrates, and nucleic acids. The methods of the invention employ MS and $(MS)^n$ methods. Currently, matrix assisted laser desorption ionization MS (MALDI/MS) and electrospray ionization MS (ESI/MS) methods are preferred. However, a variety of other MS and $(MS)^n$ techniques may be selected.

In one embodiment, the invention provides a method for quantitative analysis of a proteome using the compound of the invention. Typically, a sample is obtained from a source, as defined above. The sample may be compared to a reference protein mixture, which is obtained as a sample from the same source or may be obtained from another source. Where a sample protein mixture is to be compared to a second sample or a reference protein mixture, these mixtures are processed separately, applying identical reaction conditions, with the exception that one sample will be reacted with the compound containing heavy stable isotopes. Where samples are not to be compared, separate processing to the point of reaction with the compound(s) of the invention is not necessary, but is permitted.

Typically, the protein sample is solubilized in a suitable buffer that may contain an organic solvent. Throughout the entire procedure except the final peptide elution step, the pH of the mixture is maintained under basic conditions. Most suitably, the pH is maintained between 6.5 and 9, more preferably about 7.5 to 8.5, and most preferably about 7.2 to 7.5.

The disulfide bonds of the proteins in the sample(s) or reference mixtures are reduced to free SH groups. Optionally, this step may be combined with solubilization of the protein or protein mixture, referred to above. Suitable reducing agents include tri-n-butylphosphine (TBP), 2-mercaptoethanol, dithiothreitol, and tris-(β-carboxyethyl) phosphine. However, other suitable reducing agents may be substituted. In one embodiment, disulfide bonds in 2 mg of a protein are denatured using 8M urea, 200 mM ammonium bicarbonate, 20 mM $CaCl_2$, 5 μmole TBP, which has been pre-dissolved in 20 μL of acetonitrile (ACN) and incubated for one hour at about 37° C. In another embodiment, a protein may be incubated in 50 mM Tris buffer, 6 M guanidine-HCl, 5 mM TBP at pH 8.5 for 1 hour at 37° C. However, other concentrations of these components and/or other reducing agents, buffered to a pH in the basic range may be selected and incubated for varying lengths of times.

Free thiols (SH) are blocked using a suitable blocking reagent, e.g., methyl methane thiosulfonate (MMTS), which functions under the basic conditions provided and does not interfere with the performance of the following steps. Although MMTS is preferred, other suitable blocking reagents, including, without limitation, o-methylisourea, may be selected by one of skill in the art.

The proteins in the samples are enzymatically digested. A suitable protease for use in this method may be readily selected from among proteases that are compatible with the basic conditions and the procedure. Under certain circumstances, it may be necessary to dilute the sample mixture until any denaturing solubilizing agents in the sample are diluted to a point at which they are compatible with the activity of the protease or proteases used. In one embodiment, the protease is trypsin. In another embodiment, the protease is the endoproteinase Lys-C (commercially available, e.g., from Promega, Roche Molecular Biochemical). In still another example, a mixture of proteases that have similar activity levels at basic pH is used. Such proteases may include aminopeptidases, carboxypeptidases, among others. Alternatively, the protein mixture is subjected to more than one digestion step. For example, the protein mixture may be subjected to digestion with Lys-C, followed by digestion with trypsin. Multiple digestions are particularly desirable where the mixture is a complex mixture. One of skill in the art can readily determine whether a single digestion step, or multiple steps, are required. In yet another alternative, protein digestion may be omitted where the sample contains peptides, polypeptides or small proteins (e.g., about 500 to 5000 Da).

Suitably, the peptides are again reduced prior to being reacted with the compounds of the invention to remove the blocking reagents. The reduction step is performed using the reagents described above. In one suitable embodiment, the mixture is reduced by incubation with 5 μmole of TBP at 37° C. for one hour. However, other suitable concentrations, reagents, incubation temperatures and times may be readily substituted.

A selected compound of the invention and a corresponding isotopically heavy compound are reacted with the samples. Typically, the reference sample is labeled with the isotopically heavy compound and the experimental sample(s) are labeled with the isotopically light form of the compound. However, the labeling may be reversed. Optionally, this labeling reaction may be performed at any stage of the method, e.g., prior to any of the reduction steps.

After completion of the tagging reaction, defined aliquots of the samples labeled with isotopically different compounds (e.g., corresponding light and heavy compounds) are combined and all the subsequent steps are performed on the pooled samples. Preferably, equal amounts of each sample are pooled.

The pooled samples are washed in order to remove any non-covalently bound species. The use of the compounds of the invention permits the use of harsher washing steps than prior art reagents can withstand. For example, one suitable method utilizes 5×1 mL of 50% acetonitrile (ACN), 5×1 mL of 30% ACN, 5×1 mL of 90% ACN, 5×1 mL (non-diluted) ACN, and 10×5 mL dichloromethane. However, the concentration of ACN may be varied. Alternatively, other suitable solvents may be substituted. Examples of suitable solvents include organic solvents with polarity properties similar to acetonitrile or dichloromethane. Yet another suitable method utilizes high concentrations of organic solvents, which effectively removes any residual detergents or surfactants.

The tagged peptides are selectively retrieved by acid elution, which breaks the bond between the linker or acid labile group and the polymer to which it is covalently bond allowing the peptides tagged with the light or heavy compounds of the invention to be eluted. For example, the last washing may be eluted using 1% to 5% trifluoroacetic acid (TFA) in dichloromethane ($CH_2Cl_2$). Using the method of the invention, peptide recovery is estimated at above 75%. Suitably, recovery may be even higher, e.g., above 80%, 85%, and 90%, depending upon the sample and solvents utilized.

The isolated, derivatized peptides retrieved are then analyzed using MS techniques. Both the quantity and sequence identity of the proteins from which the tagged peptides originated can be determined by automated multistage MS. This is achieved by the operation of the mass spectrometer in a dual mode in which it alternates in successive scans between measuring the relative quantities of peptides eluting from the capillary column and recording the sequence information of selected peptides. Peptides are quantified by measuring in the MS mode the relative signal intensities for pairs of peptide ions of identical sequence that are tagged with the isotopically light or heavy forms of the compounds of the invention, respectively, and which therefore differ in mass by the mass differential encoded within the affinity-tagged reagent. Peptide sequence information is automatically generated by selecting peptide ions of a particular mass-to-charge (m/z) ratio for collision-induced dissociation (CID) in the mass spectrometer operating in the $MS^n$ mode. Using computer-searching algorithms, the resulting CID spectra are then automatically correlated with sequence databases to identify the protein from which the sequenced peptide originated. A combination of the results generated by MS and $MS^n$ analyses of the differentially labeled peptide samples therefore determines the relative quantities as well as the sequence identities of the components of the protein mixtures in a single, automated operation. Alternatively, more accurate relative quantitation may be obtained by MS analysis of the isolated peptides with the mass spectrometer operating at MS mode only [see Automated LC/MS in Example 2: Instrumentation]

Apparatuses for performing MALDI-MS and techniques for using such apparatuses are described in International Publication No. WO 93/24835, U.S. Pat. No. 5,288,644, R. Beavis and B. Chait, *Proc. Natl. Acad. Sci. USA*, 87:6873–6877 (1990); B. Chait and K. Standing, *Int. J. Mass Spectrom, Ion Phys.*, 40:185 (1981) and Mamyrin et al, *Sov. Phys. JETP*, 37:45 (1973), all of which are incorporated by reference herein. Briefly, the frequency tripled output of, e.g., a Q-switched Lumonics HY400 neodynium/yttrium aluminum garnet lawer ("Nd-YAG") (355 nm, 10-nsec output pulse) is focused by a lens (12-inch focal length) through a fused silica window onto a sample inside the mass spectrometer. The product ions formed by the laser are accelerated by a static electric potential of 30 kV. The ions then drift down a 2-m tube maintained at a vacuum of 30 µPa and their arrival at the end of the tube is detected and recorded using, e.g., a Lecroy TR8828D transient recorder. The transient records of up to 200 individual laser shots are summed together and the resulting histogram is plotted as a mass spectrum. Peak centroid determinations and data reduction can be performed using a VAX workstation or other computer system. However, other apparatuses and techniques are known and may be readily utilized for analysis of the peptides of the invention.

Reagent Kit

The invention further provides a reagent kit for the analysis of proteins by mass spectral analysis. Typically, such a kit will contain one or more compounds of the invention. Most suitably, the kit will contain a set of substantially identical, differentially labeled (isotopically light and heavy) compounds. In one desirable embodiment, the kit will contain the compounds of the invention such that the polymer portion of the compound also serves as a solid support, e.g., a bead or resin. The kit may further contain one or more proteolytic enzymes, blocking reagents, solubilizing detergent cocktails, or wash solutions. Other suitable components will be readily apparent to one of skill in the art.

The method and kit of the invention may be used for a variety of clinical and diagnostic assays, in which the presence, absence, deficiency or excess of a protein is associated with a normal or disease state. The method and kit of the invention can be used for qualitative and quantitative analysis of protein expression in cells and tissues. The method and kit can also be used to screen for proteins whose expression levels in cells or biological fluids are affected by a drug, toxin, environmental change, or by a change in condition or cell state, e.g., disease state, malignancy, site-directed mutation, gene therapy, or gene knockouts.

The following examples are provided to illustrate the invention and do not limit the scope thereof One skilled in the art will appreciate that although specific reagents and conditions are outlined in the following examples, modifications can be made which are meant to be encompassed by the spirit and scope of the invention.

EXAMPLES

Example 1

Synthesis of the Compound of the Invention

A. Preparation of Linker and Affinity Tag

A solution of maleic anhydride (0.98 g, 10.0 mmol in 15 ml of acetic acid) was added to a solution of 6-aminocaproic acid (1.31 g, 10 mmol in 5 ml of acetic acid). The resulting mixture was stirred at room temperature for two hours. After two hours, the mixture was heated to reflux (oil bath temperature about 110–120° C.) for four and a half hours. The acetic acid was removed in vacuum and 3.3 g of a light yellow solid was obtained. This solid was chromatographed (20% ethyl acetate in hexanes, then 50% ethyl acetate in hexanes) and gave 0.92 g of pure target compound (6-(2,5-dioxo-2,5-dihydro-pyrrol-1-yl)-hexanoic acid; 43% yield). This reaction is illustrated in the scheme provided below, in which acetic acid is abbreviated as HOAc.

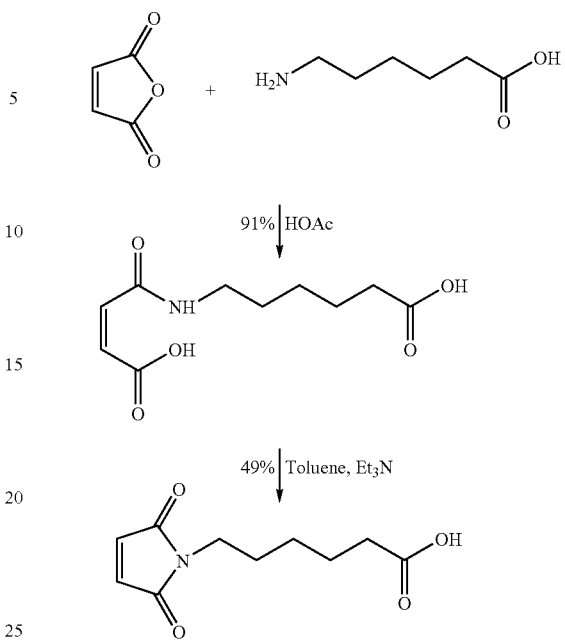

B. Preparation of Resin

The protected polymer, purchased commercially as NovaSyn TG Seiber resin (1 g, 0.15 mmol/g) was stirred in N,N-dimethylformamide (DMF) (8 mL) and then piperidine (2 mL) was added. The reaction mixture was stirred for ten minutes and then the solid was filtered and washed with methylene chloride and then dried under vacuum This dry solid was then again stirred with piperidine (2 mL) in DMF (8 mL) for another ten minutes. The thin layer chromatography (TLC) was recorded and showed no trace of the fluorenylmethyoxycarbonyl (Fmoc). The solid was then filtered and washed with methylene chloride, dried under low pressure to give about 1 g of the free amine polymer. This reaction is illustrated by the synthetic scheme below.

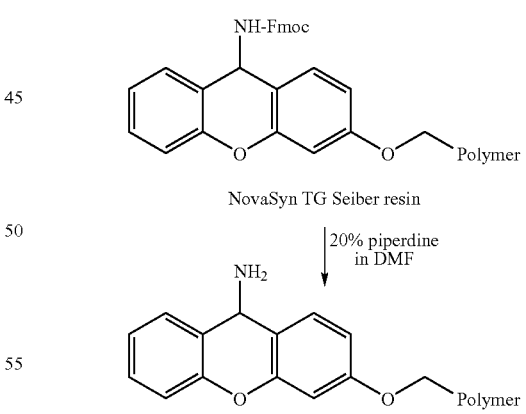

The polymer is a copolymer of polyethylene glycol and polystyrene.

C. Preparation of Compound of the Invention

The deprotected polymer (1 g, 0.15 mmol/g) synthesized as described in part B was stirred in DMF (10 mL). To this mixture was added sequentially the compound which resulted from the reaction described in part A (0.095 g, 0.45 mmol), 1-hydroxybenzotriazole (HOBT) (0.06 g, 0.45 mmol) and N,N-dicyclohexylcarbodiimide (DCC) (0.102 g, 0.5 mmol). The reaction mixture was stirred for three hours and the solid filtered and washed successively with ethyl acetate, ether and methylene chloride. The solid was then dried in vacuum and gave about 1 g of the product illustrated below (ALICE of the invention).

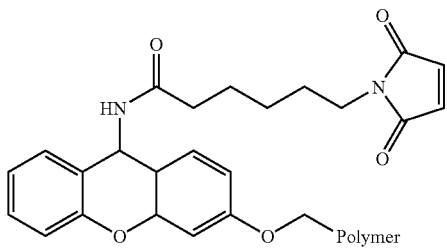

Example 2

Instrumentation

The present invention was carried out utilizing techniques and instrumentation known to those of skill in the art combined with a novel method of using the same. Specifically, data was obtained using automated LC/MS alone as well as using a novel automated 2-dimensional LC/LC/MS system using instrumentation available in the art. These instruments and methods of using the same are described below.

A. Automated LC/MS

Automated LC/MS was accomplished using a LC/MS MicroMass Q-ToF$^2$ mass spectrometer (Micromass, Manchester, UK) equipped with an ABI 140 C. microgradient syringe pump system (Applied Biosystems, Framingham, Mass.). The sample was injected onto a strong cation exchange (SCX) column, a 100 μm×6 cm IntegraFrit column (New Objectives, Woburn, Mass.) packed with PolySULFOETHYL A, 12 μm, 300 Å (PolyLC Inc., Columbia, Md.). The sample was then eluted onto a RP-C18 column, a 75 μm×10 cm PicoFrit column (New Objectives, Woburn, Mass.) packed with YMC-Gel 10 μM C18 beads (YMC Inc., Wilmington, N.C.) using a solution of 500 mM KCl in 0.1 M acetic acid. The RP-C18 column was equilibrated with 96% acetic acid/4% ACN and then the following gradient was run: (i) 4–65% RP-B over 75 minutes, (ii) 65–98% RP-B over the next 7 minutes, (iii) a hold at 98% RP-B for 5 minutes, and (iv) 98–1% RP-B over the next 3 minutes at 250 μL/min. Mobile-phase buffers were for RP-A: 0.1 M acetic acid, 1% ACN and RP-B: 0.1 M acetic acid, 90% ACN. Data was acquired in the MS mode only.

B. Automated 2D-LC/MSIMS

Figure 1B:
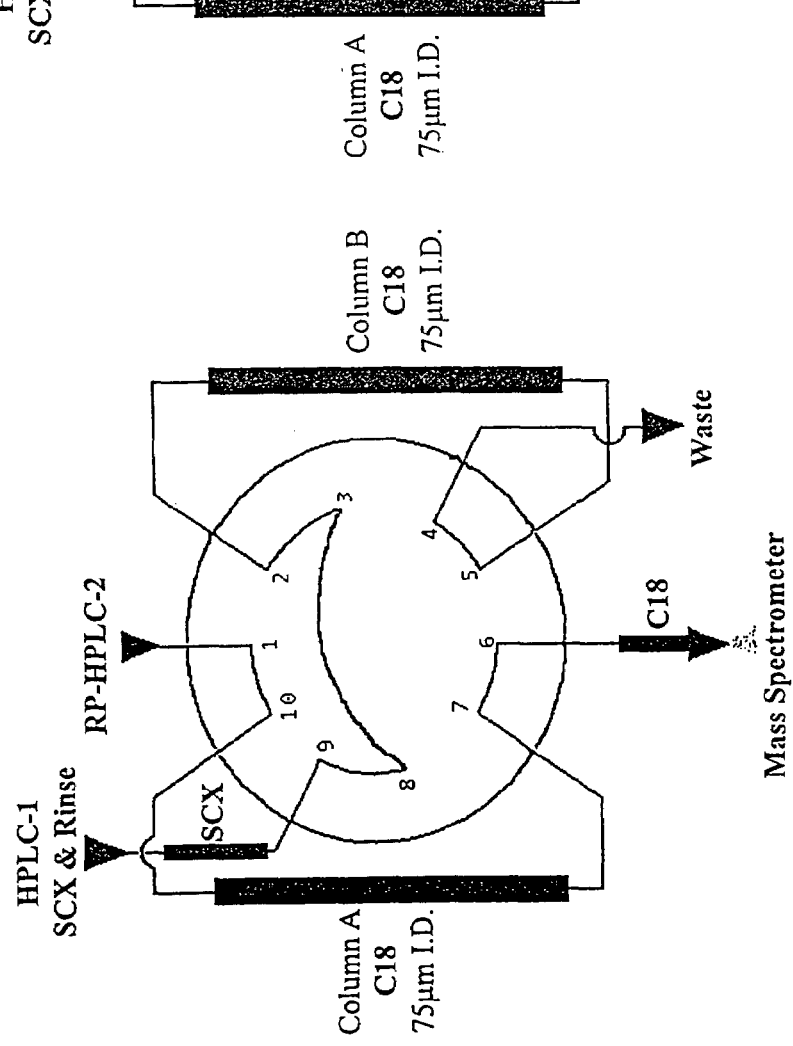

Automated 2D-LC/MS/MS was accomplished using the system as shown in FIGS. 1A and 1B. Specifically, a 2D LC-MS/MS Finnigan LCQ Deca ion trap mass spectrometer was fitted with an Applied Biosystems 140C microgradient syringe pump system (Applied Biosystems, Framingham, Mass.), as the reverse phase pump (RP), and an Agilent 1100 series binary pump, as the strong cation exchange (SCX) and desalting pump. The pumps were attached to a VICI 10 port microbore two-position valve with a microelectric actuator (Valco Instruments CO Inc., Houston, Tex.). A strong cation exchange column, 50×1 mm PolySULFOETHYL A (PolyLC Inc., Columbia, Md.), was attached to port 9 and two 75 mm×10 cm IntegraFrit columns (New Objectives, Woburn, Mass.) packed with YMC-Gel 10 μm C18 beads (YMC Inc., Wilmington, N.C.) were attached between ports 2 and 5, and 7 and 10, respectively. Another 75 μm×3 cm C18 column packed in a PicoFrit column (New Objectives) was placed in between the titanium voltage union and the heated capillary of the mass spectrometer, to restore a loss of resolution from the valve and the titanium union.

Automation between the mass spectrometer, pumps and valve was accomplished using contact closures. First, the sample was loaded onto the SCX column using a Rheodyne injection valve (Rheodyne, Rohnert Park, Calif.) with the port valve at position 10 as shown in FIG. 1B so that any unbound peptides would bind to the RP-18 column and elute in fraction 0. With this dual C18 column design, while one RP-C18 column (column A in FIG. 1A) is being on-line with the mass spectrometer for peptide separation, the other C18 column (Column B in FIG. 1A) is being regenerated, loaded with peptide sample eluted from the SCX column and desalted. After each HPLC gradient run is completed, the positions of the two RP-C18 columns were switched over using the two-position ten-port valve (FIG. 1B) so that the time delay for equilibrating, sample loading from SCX and desalting was effectively eliminated. Peptide factions were eluted from the SCX column onto one RP-C18 column using the following salt steps: (i) 5%, (ii) 10%, (iii) 15%, (iv) 20%, (v) 30%, (vi) 40%, (vii) 50%, (viii) 65%, (ix) 85%, (x) 98%, (xi) 98%, (xii) 98%, and (xiii) 98%, SCX-B:SCX-A, for 10 minutes at 1 μL/min. Before each elution, 100% SCX-A was flowed at 1 μL/min for 20 minutes to equilibrate the RP C18 column and after each salt elution, 100% SCX-A was flowed at 1 μL/min for 20 minutes for elutions (i) to (iv), 25 minutes for elutions (v) and (vi), 30 minutes for elutions (vii) and (viii), and 35 minutes for elutions (ix) to (xiii). The flow was then slowed down to 200 nL/min for the remainder of time to rinse the salt from the RP C18 column. Peptides were eluted from one C18 column into the mass spectrometer using a linear RP gradient: a) 1–65% RP-B over 75 minutes, b) 65–98% RP-B over the next 7 minutes, c) a hold at 98% RP-B for 5 minutes, and d) 98–1% RP-B over the next 3 minutes at 400 nL/min. Mobile-phase buffers were, RP-A: 0.1 M acetic acid, 1% ACN; RP-B: 0.1 M acetic acid, 90% ACN; SCX-A: 0.1 M acetic acid, 1% ACN; SCX-B: 500 mM KCl. (FIGS. 1A and 1B).

Example 3

Preparation of Proteomes for MS Analysis 2 mg of bovine serum albumin (BSA) were solubilized in 200 μL of 8 M urea, 200 mM ammonium bicarbonate, and 20 mM $CaCl_2$. 5 μmole of tributyl phosphine (TBP) pre-dissolved in 20 μL of acetonitrile (ACN) was added into the solubilized protein mixture and the resulting solution was incubated at 37° C. for one hour. To the protein mixture was added 11 μmoles of MMTS and the mixture was vortexed for 10 minutes. The protein solution was diluted 1:1 with 100 mM ammonium bicarbonate and 40 μg of Lys-C (2% w/w) were added. This mixture was then incubated at 37° C. for 5 hours. The resulting solution was diluted 1:1 with water and then proteins were further digested with trypsin (2% w/w) at 37° C. for 15 hours. The resulting peptide solution was dried and then reconstituted with 50% acetonitrile/200 mM sodium phosphate (pH 7.2). Disulfide bonds on the cysteine-containing peptides were reduced with TBP (5 μmoles) at 37° C. for one hour. Then 50 mg of the ALICE resin (about 11.5 μmole reactive sites) was added into the peptide solution and the solution vortexed for 1 hour at room temperature. The solutions were combined and loaded onto a column (glass type with teflon cockstop) and the resin was washed with the following solvent in sequence: 1) 5×1 mL of 50% ACN, 2) 5×1 mL of 30% ACN, 3) 5×1 mL of 90% ACN, 4) 5×1 mL of pure ACN, 5) 10×5 mL of dichloromethane (DCM).

Cysteine-containing peptides were then eluted from the resin with 5% TFA in DCM using continuous flow methodology. The resulting peptide solution was dried and reconstituted with 1% acetic acid in water. The reconstituted peptide solution was directly subjected to automated 2D-LC/MS/MS analysis (as described above) without further treatment. MS analysis combined with database searching yielded both identities and quantities of the proteins.

Samples were taken from the mixture before and after acid elution for MS analysis to compare the overall recovery of cysteine-containing peptides with or without using the ALICE approach. The results are provided below, with reference to the following published sequence of bovine serum albumin (using single letter amino acid code):

```
SEQ ID NO. 1:
  1  MKWVTFISLL LLFSSATYSRG VFRRDTHKSE IAHRFKDLGE

41  EHFKGLVLIA FSQYLQQCPF DEHVKLVNEL TEFAKTCVAD

81  ESHAGCEKSL HTLFGDELCK VASLRETYGD MADCCEKQEP

121  ERNECFLSHK DDSPDLPKLK PDPNTLCDEF KADEKKFWGK

161  YLYEIARRHP YFYAPELLYY ANKYNGVFQE CCQAEDKGAC

201  LLPKIETMRE KVLTSSARQR LRCASIQKFG ERALKAWSVA

241  RLSQKFPKAE FVEVTKLVTD LTKVHKECCH GDLLECADDR

281  ADLAKYICKN QDTISSKLKE CCDKPLLEKS HCIAEVEKDA

321  IPENLPPLTA DFAEDKDVCK NYQEAKDAFL GSFLYEYSRR

361  HPEYAVSVLL RLAKEYEATL EECCAKDDPH ACYSTVFDKL

401  KHLVDEPQNL IDQNCDQFEK LGEYGFQNAL IVRYTRKVPQ

441  VSTPTLVEVS RSLGKVGTRC CTKPESERMP CTEDYLSLIL

481  NRLCVHEKT  PVSEKVTKCC TESLVNRRPC FSALTDETY

521  VPKAFDEKLF TFHADICTLP DTEKQIKKQT ALVELLKHKP

561  KATEEQLKTV MENFVAFVDK CCAADDKEAC FAVEGPKLVV

601  STQTALA
```

Peptides identified from peptide mixtures before and after using ALICE for isolation of cysteine-containing peptides

| Peptides identified by LC-MS/MS and database searching from the sample after enzymatic digestion but before reaction with ALICE (including both cysteine containing and non-cysteine containing peptides) Position, based on SEQ ID NO. 1 | | Peptides identified by LC-MS/MS and database searching from the final sample eluted from the ALICE resin (exclusively cysteine-containing peptides) Position, based on SEQ ID NO. 1* | |
|---|---|---|---|
| 508–523 | 76–88 | 508–523 | 460–468 |
| 402–412 | 437–451 | 89–100 | 483–489 |
| 106–117 | 89–100 | 267–280 | 123–130 |
| 198–204 | 298–309 | 106–117 | 286–297 |
| 310–318 | 267–280 | 581–587 | 499–507 |
| 161–167 | 375–386 | 45–65 | 199–204 |
| 123–130 | 499–507 | 310–318 | 198–204 |
| 286–297 | 360–371 | 76–88 | 300–309 |
| 460–468 | 562–568 | 588–597 | 387–399 |
| 421–433 | 123–138 | 52–65 | 375–386 |
| 529–544 | 95–100 | 139–151 | 319–340 |
| 300–309 | 588–597 | 413–420 | 223–228 |
| 413–420 | 533–544 | 529–544 | 469–482 |
| 598–607 | 548–557 | | |
| 35–44 | 172–183 | | |
| 45–65 | 319–340 | | |
| 347–359 | 469–482 | | |
| 341–353 | 435–451 | | |
| 354–359 | 413–424 | | |
| 168–180 | 387–399 | | |
| 361–371 | 66–75 | | |
| 581–597 | 549–557 | | |
| 569–580 | 139–151 | | |

*Two highlighted cysteine-containing peptides: CASIQK (residues 223–228) and LCVLHEK (residues 483–489) were only detected from the final sample eluted from the ALICE resin.

This study demonstrated that nonspecific binding associated with the use of conventional reagents is not a problem using the compounds of the invention, since all the peptides eluted from the resin after washing are exclusively cysteine-containing peptides. This is because the compounds of the invention permit the use of much more stringent washing conditions, as compared to conventional ICAT reagents. Thus, the compounds of the invention provide lower "noise", better dynamic range and sensitivity in subsequent MS analysis.

More specifically, in this study, 33 out of 35 cysteines were captured. Only one Cys-containing peptide, YNGVFQECCQAEDK (residues 184–197 of SEQ ID NO.1) was not recovered either before or after isolation CASIQK (residues 223–228 of SEQ ID NO.1) and LCVLHEK (residues 483–489 of SEQ ID NO.1) were only seen after isolation. This is likely due to the better dynamic range and sensitivity provided by the compound of the invention. Although not measured, overall recovery percentage is anticipated to be more than 75%. Steric hindrance in the capturing step is not a problem, since the peptides containing more than one cysteine were all uniformly modified by ALICE, the model compound of the invention. From all the CID experiments, no fragments observed were from the ALICE label, indicating that the compound would not interfere with the MS/MS experiments and subsequent protein identification by fragment-ion based database searching.

Example 4

Capturing Cysteine-Containing Peptides Using Alice, Simple Protein Mixtures, and Automated LC/MS and 2D-LC/MS Two mixtures were prepared, each containing eight proteins. The following table illustrates the composition of these mixtures.

Composition of two protein mixtures

| Protein Name | Protein Mixture A (nmol) | Protein Mixture B (nmol) |
| --- | --- | --- |
| Lysozyme | 10 | 50 |
| α-lactalbumin | 50 | 10 |
| Ovalbumin | 25 | 50 |
| Catalase | 50 | 25 |
| β-lactoglobulin | 38 | 50 |
| BSA | 50 | 38 |
| Ribonuclease | 50 | 50 |
| Trypsinogen | 50 | 50 |

Protein mixture A and protein mixture B (323 nmol of total protein were solubilized, respectively, in 325 μL of 6 M urea, 5% 3-[(3-cholamidopropyl)-dimethylammonio]-1-propanesulfonate (CHAPS), and 50 MM Tris HCl. 11.3 μmole of tributyl phosphine (TBP) pre-dissolved in 6.3 μL of isopropanol (IPA) was added to each solubilized protein mixture and the resulting solutions were incubated at 37° C. for one hour. To each protein mixture was added 200 μL of 50 mM Tris-HCl (pH 8.0) and 34 μmol of methanethiosulfonate (MMTS) predissolved in 3.5 μL of IPA, and the mixtures were reacted for 30 minutes. Each protein solution was diluted four times with 50 mM Tris-HCl (pH 8.0) and digested with trypsin (5% w/w) at 37° C. for 16 hours. From the total peptide mixtures, 42% (21% from each mixture) was retained for future work, and the remaining 58% (187 nmol total protein) was dried and then reconstituted with 1.5 mL of 60% acetonitrile (ACN)/40% 100 mM Tris-HCl (pH 7.0). Disulfide bonds on the cysteine-containing peptides were reduced by TBP (18.7 μmol) at 37° C. for one hour. Each solution was then vacuum concentrated for 10 minutes to remove excess TBP and ACN, and reconstituted to the previous volume using ACN. To each solution was added 55 μmol of either light or heavy ALICE resins (3×TBP molar equivalent) and the solutions were stirred for 1 hour at room temperature. The reactions were quenched by the addition of β-mercaptoethanol (BME) to a final concentration of 1%.

The protein mixtures were then combined and loaded onto a column (fritted glass type with Teflon cockstop) and the resin was washed with the following solvent in sequence: (i) 50 mL of a 50:50 ACN:water solution, (ii) 50 mL of pure ACN, (iii) 50 mL of a 50:50 ACN:dichloromethane (DCM) solution, and (iv) 50 mL of pure DCM.

Cysteine-containing peptides were isolated by elution with 3×5 mL of 5% TFA in DCM using continuous flow methodology, 15 minute incubations with intermittent shaking, then 15 mL of continuous flow. The resulting peptide solution was dried and reconstituted with 2% ACN in 1% acetic acid/water. The reconstituted peptide solution was directly subjected to HPLC-MS MicroMass Q-ToF$^2$ instrument (MicroMass, Manchester, UK) and 2D-LC-MS/MS (Finnigan LCQ Deca, Finnigan Corporation, San Jose, Calif.) analysis without further treatment. These analyses, combined with database searching, yielded both identities and quantities of the proteins. The chemical reactions for the isolation of cysteine-containing peptides are illustrated in the following scheme.

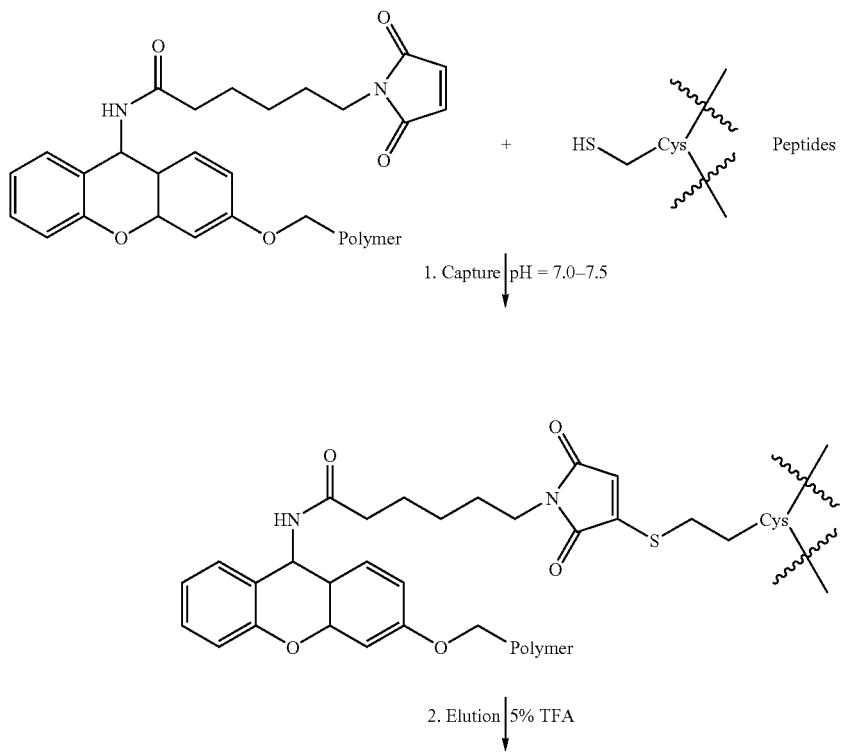

-continued

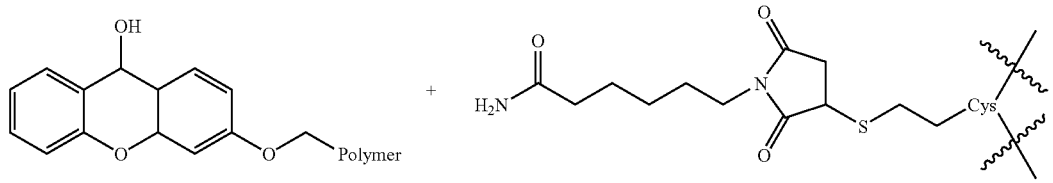

The results of the mass-spectrometric analysis are provided in the following table. In this table, M#=oxidized methionine residue; C*=light and heavy ALICE labeled cysteine residue.

TABLE

Sequence identification and quantitation of the components of a protein mixture using ALICE.

| Protein Name | Peptide Mass// Charge State | Peptide Sequence identified/SEQ ID NO: | Obs'd Ratio/ Mean ± SD | Exp. Ratio | % Error |
|---|---|---|---|---|---|
| α-lactoalbumin | 432.20//2 | (K)C*EVFR(E) SEQ ID NO: 3 | 4.97 | 5 | 0.6 |
| β-lactoglobulin/ | 1107.84//3 | (K)YLLFC*M#ENSAEPEQSLVC*QC*LVR(T): SEQ ID NO: 4 | 0.76 0.76 ± 0.01 | 0.76 | 0.3 |
| | 934.94//2 | (R)LSFNPTQLEEQC*HI(-): SEQ ID NO: 5 | 0.77 | | |
| Catalase | 654.34//2 | (R)LC*ENIAGHLK(D) SEQ ID NO: 6 | 2.1 0.02 ± 0.09 | 2 | 1 |
| | 436.56//3 | (R)LC*ENIAGHLK(D): SEQ ID NO: 6 | 1.93 | | |
| | 979.00//2 | (R)LGPNYLQIPVNC*PYR(A): SEQ ID NO: 7 | 2.01 | | |
| Lysozyme | 1062.49//1 | (R)C*ELAAAM#K(R): SEQ ID NO: 8 | 0.2 | 0.2 | 0.2 |
| Ovalbumin | 739.80//2 | (A)SM#EFCFDVFK(E): SEQ ID NO: 9 | 0.61 0.58 ± 0.05 | 0.5 | 16 |
| | 700.85//2 | (R)ADHPFLFC*IK(H): SEQ ID NO: 10 | 0.6 | | |
| | 467.57//3 | (R)ADHPFLFC*IK(H): SEQ ID NO: 10 | 0.52 | | |
| | 838.44//2 | (R)YPILPEYLQC*VK(E) SEQ ID NO: 11 | 0.59 | | |
| Ribonuclease | 1189.08//2 | (K)HIIVAC*EGNPYVPVHFDASV(-) SEQ ID NO: 12 | 1.08 1.00 ± 0.11 | 1 | 0.4 |
| | 793.06//3 | (K)HIIVAC*EGNPYVPVHFDASV(-) SEQ ID NO: 12 | 1.16 | | |
| | 595.04//4 | (K)HIIVAC*EGNPYVPVHFDASV(-) SEQ ID NO: 12 | 1.17 | | |
| | 706.60//4 | (R)C*KPVNTFVHESLADVQAVC*SQK(N) SEQ ID NO: 13 | 0.89 | | |
| | 922.40//2 | (A)CEGNPYVPVHFDASV(-) aa 6-22 of SEQ ID NO: 12 | 1.03 | | |
| | 608.63//3 | (F)VHESLADVQAVCSQK(N) aa 6-24 of SEQ ID NO: 12 | 0.96 | | |
| | 865.5//1 | (K)HIIVAC*(E) aa 1-8 of SEQ ID NO: 14 | 1.03 | | |

TABLE-continued

Sequence identification and quantitation of
the components of a protein mixture using ALICE.

| Protein Name | Peptide Mass// Charge State | Peptide Sequence identified/SEQ ID NO: | Obs'd Ratio/ Mean ± SD | Exp. Ratio | % Error |
|---|---|---|---|---|---|
| | 433.25//2 | (K)HIIVAC*(E)<br>aa 1–8 of SEQ ID NO: 14 | 0.9 | | |
| | 1239.5//1 | (Y)STM#SITDC*R(E)<br>SEQ ID NO: 14 | 0.9 | | |
| | 620.25//2 | (Y)STM#SITDC*R(E)<br>SEQ ID NO: 14 | 0.84 | | |
| Trypsinogen | 580.3//2 | (A)PILSDSSC*K(S)<br>aa 5–15 of SEQ ID NO: 15 | 0.87<br>1.02 ± 0.10 | 1 | 2 |
| | 1230.61//1 | (K)APILSDSSC*K(S)<br>aa 4–15 of SEQ ID NO: 15 | 1.01 | | |
| | 615.80//2 | (K)APILSDSSC*K(S)<br>aa 4–15 of SEQ ID NO: 15 | 1.18 | | |
| | 892.95//2 | (K)C*LKAPILSDSSC*K(S)<br>SEQ ID NO: 15 | 1.02 | | |
| | 595.63//3 | (K)C*LKAPILSDSSC*K(S)<br>SEQ ID NO: 15 | 1.04 | | |
| | 958.41//2 | (K)DSC*QGDSGGPVVC*SGK(L)<br>SEQ ID NO: 16 | 0.98 | | |
| BSA | 1141.6//1 | (C)C*TESLVNR(R)<br>aa 497–506 of SEQ ID NO: 1 | 1.5<br>1.35 ± 0.10 | 1.32 | 2.3 |
| | 566.25//2 | (C)C*TESLVNR(R)<br>aa 497–506 of SEQ ID NO: 1 | 1.28 | | |
| | 623.35//2 | (H)TLFGDELC*K(V)<br>aa 92–102 of SEQ ID NO: 1 | 1.21 | | |
| | 1194.02//2 | (K)C*C*AADDKEAC*FAVEGPK(L)<br>aa 577–595 of SEQ ID NO: 1 | 1.24 | | |
| | 796.35//3 | (K)C*C*AADDKEAC*FAVEGPKQ(L)<br>aa 577–595 of SEQ ID NO: 1 | 1.23 | | |
| | 722.83//2 | (K)C*C*TESLVNR(R)<br>aa 496–506 of SEQ ID NO: 1 | 1.34 | | |
| | 650.30//3 | (K)DDPHAC*YSTVFDKLK(H)<br>aa 386–402 of SEQ ID NO: 1 | 1.35 | | |
| | 630.80//2 | (K)EAC*FAVEGPK(L)<br>aa 584–595 of SEQ ID NO: 1 | 1.3 | | |
| | 533.25//3 | (K)EC*C*DKPLLEK(S)<br>aa 300–311 of SEQ ID NO: 1 | 1.41 | | |
| | 911.50//1 | (K)GAC*LLPK(I)<br>aa 198–206 of SEQ ID NO: 1 | 1.48 | | |
| | 638.80//2 | (K)LFTHADIC*(T)<br>aa 525–535 of SEQ ID NO: 1 | 1.35 | | |
| | 638.80//2 | (K)LFTFHADIC*(T)<br>aa 525–535 of SEQ ID NO: 1 | 1.51 | | |
| | 613.65//3 | (K)LKEC*C*DKPLLEK(S)<br>aa 298–311 of SEQ ID NO: 1 | 1.51 | | |
| | 577.28//3 | (K)LKPDPNTLC*DEFK(A)<br>aa 139–153 of SEQ ID NO: 1 | 1.21 | | |

TABLE-continued

Sequence identification and quantitation of
the components of a protein mixture using ALICE.

| Protein Name | Peptide Mass// Charge State | Peptide Sequence identified/SEQ ID NO: | Obs'd Ratio/ Mean ± SD | Exp. Ratio | % Error |
|---|---|---|---|---|---|
| | 786.89//2 | (K)SLHTLFGDELC*K(V)<br>aa 89–102 of SEQ ID NO: 1 | 1.35 | | |
| | 524.92//3 | (K)SLHTLFGDELC*K(V)<br>aa 89–102 of SEQ ID NO: 1 | 1.35 | | |
| | 885.37//2 | (K)TC*VADESHAGC*EK(S)<br>aa 76–90 of SEQ ID NO: 1 | 1.52 | | |
| | 590.58//3 | (K)TC*VADESHAGC*EK(S)<br>aa 76–90 of SEQ ID NO: 1 | 1.52 | | |
| | 591.62//3 | (K)VTKC*C*TESLVNR(R)<br>aa 493–506 of SEQ ID NO: 1 | 1.19 | | |
| | 798.86//2 | (K)YIC*DNQDTISSK(L)<br>aa 286–299 of SEQ ID NO: 1 | 1.36 | | |
| | 1027.43//2 | (K)YNGVFQEC*C*QAEDK(G)<br>aa 184–199 of SEQ ID NO: 1 | 1.2 | | |
| | 859.43//1 | (R)C*ASIQK(F)<br>aa 223–230 of SEQ ID NO: 1 | 1.46 | | |
| | 430.21//2 | (R)C*ASIQK(F)<br>aa 223–230 of SEQ ID NO: 1 | 1.3— | | |
| | 1051.56//1 | (R)LC*VLHEK(T)<br>aa 481–488 of SEQ ID NO: 1 | 1.35 | | |
| | 526.284//2 | (R)LC*VLHEK(T)<br>aa 481–488 of SEQ ID NO: 1 | 1.27 | | |
| | 947.45//2 | (R)M#PC*TEDYLSLILNR(L)<br>aa 468–482 of SEQ ID NO: 1 | 1.36 | | |
| | 631.97//3 | (R)M#PC*TEDYLSLILNR(L)<br>aa 468–482 of SEQ ID NO: 1 | 1.25 | | |
| | 1027.97//2 | (R)NEC*FLSHKDDSPDLPK(L)<br>aa 123–140 of SEQ ID NO: 1 | 1.27 | | |
| | 1017.50//2 | (R)RPC*FSALTPDETYVPK(A)<br>aa 505–521 of SEQ ID NO: 1 | 1.41 | | |
| | 678.672//3 | (R)RPC*FSALTPDETYVPK(A)<br>aa 505–521 of SEQ ID NO: 1 | 1.39 | | |

This study demonstrated that quantification by ALICE is accurate after taking into account the following factors: isotopic impurity of the heavy ALICE; different elution profile of the same peptides modified by heavy and light ALICE; non-specific enzymatic cleavage. This improved quantitation accuracy by ALICE is even more evident when multiple cysteine-containing peptides are present. Peptides without any cysteine residue were rarely seen in the final captured peptide mixture since more stringent washing conditions completely removed non-specifically bound species. Furthermore, the use of large amounts of organic solvents also minimized the loss of peptides throughout the procedure. Finally, simplification of the peptide mixture by isolating cysteine-containing peptides in combination with the novel automated 2D-LC/MS design increase the overall sample loading capacity, the speed of sample analysis and the dynamic range and sensitivity of the MS analysis of protein mixtures. This experiment also further confirmed that reaction between ALICE and cysteine-containing peptides is efficient and stoichiometric and the effect of steric hindrance is not a concern since peptides with more than one cysteine residue were modified completely by ALICE. For example, a tryptic peptide with three cysteine residues derived from lysozyme (NLC*NIPC*SALLSSDITASVNC*AK, SEQ ID NO:2) was uniformly labeled with either heavy or light ALICE (the mass difference (not shown) between this heavy and light mass pairs is exactly 30 Da). Both light and heavy ALICE labeled peptides were effectively picked by the automated 2D-LC/LC/MS system for MS/MS analysis even though the peak intensity for the light ALICE labeled peptide is very low. Subsequent database searching identified the peptide as NLC*NIPC*SALLSSDITASVNC*AK [SEQ ID NO:2] with cysteine residues modified by light and heavy ALICE, respectively.

All publications cited in this specification are incorporated herein by reference herein. While the invention has been described with reference to a particularly preferred embodiment, it will be appreciated that modifications can be made without departing from the spirit of the invention. Such modifications are intended to fall within the scope of the appended claims.

---

What is claimed is:

1. A compound useful for capturing cysteine-containing peptides, comprising a thiol-specific reactive group attached to a non-biological polymer via a linker;
wherein the thiol-specific reactive group is a maleimide group, an α-haloacetyl group, or an α-, β-conjugated double bond structure.

2. The compound according to claim 1, wherein the linker contains a substitution of at least six atoms with a stable isotope.

3. The compound according to claim 2, wherein the stable isotope is deuterium.

4. The compound according to claim 1, wherein the linker contains ten stable isotopes.

5. A reagent kit for the analysis of proteins by mass spectrometry analysis, said kit comprising the compound of claim 1.

6. The reagent kit of claim 5 which comprises a set of compounds of claim 1, said set of compounds are differentially labeled with stable isotopes.

7. The reagent kit of claim 6 further comprising one or more proteolytic enzymes for use in digestion of proteins to be analyzed.

8. The compound of claim 1, wherein the thiol-specific reactive group is a maleimide group.

9. The compound of claim 8, wherein the thiol-specific reactive group has a structure represented by the formula:

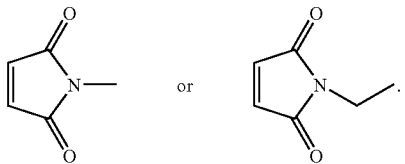

10. The compound of claim 1, wherein the thiol-specific reactive group is an α-haloacetyl group.

11. The compound of claim 10, wherein the thiol-specific reactive group has a structure represented by the formula:

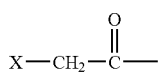

wherein X is iodine, bromine or chlorine.

12. The compound of claim 1, wherein the thiol-specific reactive group is an α-, β-conjugated double bond structure.

13. The compound of claim 12, wherein the thiol-specific reactive group has a structure represented by the formula:

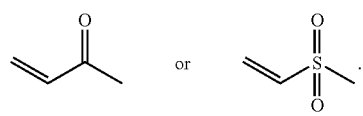

14. The compound of claim 1, wherein the polymer covalently bound to the linker has a structure represented by one of the following formulae:

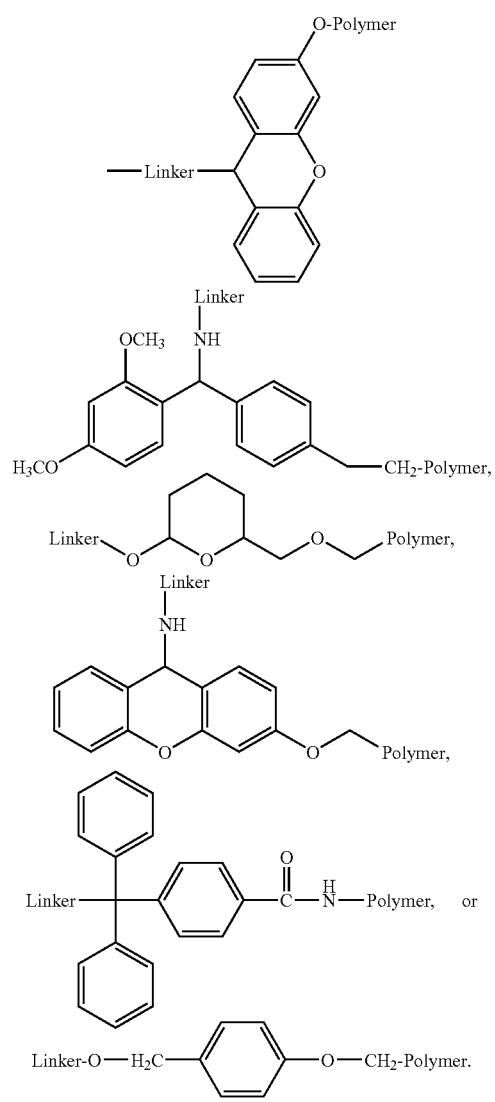

15. The compound of claim 1, wherein the polymer covalently bound to the linker has a structure represented by the formula:

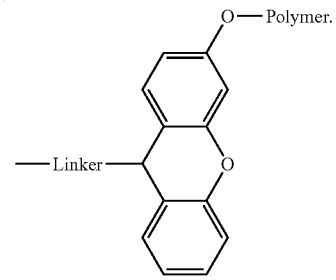

16. The compound of claim 1 having a structure represented by the formula:

A1-Linker-A2-Polymer;

or the formula:

A1-Linker-Polymer;

wherein A1 represents the thiol specific reactive group and wherein A2 represents an acid labile group.

* * * * *

SEQUENCE LISTING

<160> NUMBER OF SEQ ID NOS: 16

<210> SEQ ID NO 1
<211> LENGTH: 604
<212> TYPE: PRT
<213> ORGANISM: Bovine Serum Albumin

<400> SEQUENCE: 1

```
Met Lys Trp Val Thr Phe Ile Ser Leu Leu Leu Phe Ser Ser Ala
1               5                   10                  15

Thr Tyr Ser Arg Gly Val Phe Arg Arg Asp Thr His Lys Ser Glu Ile
                20                  25                  30

Ala His Arg Phe Lys Asp Leu Gly Glu Glu His Phe Lys Gly Leu Val
            35                  40                  45

Leu Ile Ala Phe Ser Gln Tyr Leu Gln Gln Cys Pro Phe Asp Glu His
        50                  55                  60

Val Lys Leu Val Asn Glu Leu Thr Glu Phe Ala Lys Thr Cys Val Ala
65                  70                  75                  80

Asp Glu Ser His Ala Gly Cys Glu Lys Ser Leu His Thr Leu Phe Gly
                85                  90                  95

Asp Glu Leu Cys Lys Val Ala Ser Leu Arg Glu Thr Tyr Gly Asp Met
            100                 105                 110

Ala Asp Cys Cys Glu Lys Gln Glu Pro Glu Arg Asn Glu Cys Phe Leu
        115                 120                 125

Ser His Lys Asp Asp Ser Pro Asp Leu Pro Lys Leu Lys Pro Asp Pro
130                 135                 140

Asn Thr Leu Cys Asp Glu Phe Lys Ala Asp Glu Lys Lys Phe Trp Gly
145                 150                 155                 160

Lys Tyr Leu Tyr Glu Ile Ala Arg Arg His Pro Tyr Phe Tyr Ala Pro
                165                 170                 175

Glu Leu Leu Tyr Tyr Ala Asn Lys Tyr Asn Gly Val Phe Gln Glu Cys
            180                 185                 190

Cys Gln Ala Glu Asp Lys Gly Ala Cys Leu Leu Pro Lys Ile Glu Thr
        195                 200                 205

Met Arg Glu Lys Val Leu Thr Ser Ser Ala Arg Gln Arg Leu Arg Cys
            210                 215                 220

Ala Ser Ile Gln Lys Phe Gly Glu Arg Ala Leu Lys Ala Trp Ser Val
225                 230                 235                 240

Ala Arg Leu Ser Gln Lys Phe Pro Lys Ala Glu Phe Val Glu Val Thr
                245                 250                 255

Lys Leu Val Thr Asp Leu Thr Lys Val His Lys Glu Cys Cys His Gly
            260                 265                 270

Asp Leu Leu Glu Cys Ala Asp Asp Arg Ala Asp Leu Ala Lys Tyr Ile
        275                 280                 285

Cys Lys Asn Gln Asp Thr Ile Ser Ser Lys Leu Lys Glu Cys Cys Asp
    290                 295                 300

Lys Pro Leu Leu Glu Lys Ser His Cys Ile Ala Glu Val Glu Lys Asp
305                 310                 315                 320
```

-continued

```
Ala Ile Pro Glu Asn Leu Pro Pro Leu Thr Ala Asp Phe Ala Glu Asp
            325                 330                 335

Lys Val Cys Lys Asn Tyr Gln Glu Ala Lys Asp Ala Phe Leu Gly Ser
            340                 345                 350

Phe Leu Tyr Glu Tyr Ser Arg Arg His Pro Glu Tyr Ala Val Ser Val
            355                 360                 365

Leu Leu Arg Leu Ala Lys Glu Tyr Glu Ala Thr Leu Glu Glu Cys Cys
370                 375                 380

Ala Lys Asp Asp Pro His Ala Cys Tyr Ser Thr Val Phe Asp Lys Leu
385                 390                 395                 400

Lys His Leu Val Asp Glu Pro Gln Asn Leu Ile Asp Gln Asn Cys Asp
            405                 410                 415

Gln Phe Glu Lys Leu Gly Glu Tyr Gly Phe Gln Asn Ala Leu Ile Val
            420                 425                 430

Arg Tyr Thr Arg Lys Val Pro Gln Val Ser Thr Pro Thr Leu Val Glu
            435                 440                 445

Val Ser Arg Ser Leu Gly Lys Val Gly Thr Arg Cys Cys Thr Gly Pro
450                 455                 460

Glu Ser Glu Arg Met Pro Cys Thr Glu Asp Tyr Leu Ser Ile Leu Asn
465                 470                 475                 480

Arg Leu Cys Val His Glu Lys Thr Pro Val Ser Glu Lys Val Thr Lys
            485                 490                 495

Cys Cys Thr Glu Ser Leu Val Asn Arg Arg Pro Cys Phe Ser Ala Leu
            500                 505                 510

Thr Asp Glu Thr Tyr Val Pro Lys Ala Phe Asp Glu Lys Leu Phe Thr
            515                 520                 525

Phe His Ala Asp Ile Cys Thr Leu Pro Asp Thr Glu Lys Gln Ile Lys
            530                 535                 540

Lys Gln Thr Ala Leu Val Glu Leu Leu Lys His Lys Pro Lys Ala Thr
545                 550                 555                 560

Glu Glu Gln Leu Lys Thr Val Met Glu Asn Phe Val Ala Phe Val Asp
            565                 570                 575

Lys Cys Cys Ala Ala Asp Asp Lys Glu Ala Cys Phe Ala Val Glu Gly
            580                 585                 590

Pro Lys Leu Val Val Ser Thr Gln Thr Ala Leu Ala
            595                 600
```

```
<210> SEQ ID NO 2
<211> LENGTH: 23
<212> TYPE: PRT
<213> ORGANISM: Peptide from Lysozyme

<400> SEQUENCE: 2

Asn Leu Cys Asn Ile Pro Cys Ser Ala Leu Leu Ser Ser Asp Ile Thr
1               5                   10                  15

Ala Ser Val Asn Cys Ala Lys
            20
```

```
<210> SEQ ID NO 3
<211> LENGTH: 7
<212> TYPE: PRT
<213> ORGANISM: Peptide from alpha-lactoalbumin

<400> SEQUENCE: 3

Lys Cys Glu Val Phe Arg Glu
1               5
```

```
<210> SEQ ID NO 4
<211> LENGTH: 25
<212> TYPE: PRT
<213> ORGANISM: Peptide from beta-lactoglobulin

<400> SEQUENCE: 4

Lys Tyr Leu Leu Phe Cys Met Glu Asn Ser Ala Glu Pro Glu Gln Ser
1               5                   10                  15

Leu Val Cys Gln Cys Leu Val Arg Thr
            20                  25

<210> SEQ ID NO 5
<211> LENGTH: 15
<212> TYPE: PRT
<213> ORGANISM: Peptide from beta-lactoglobulin

<400> SEQUENCE: 5

Arg Leu Ser Phe Asn Pro Thr Gln Leu Glu Glu Gln Cys His Ile
1               5                   10                  15

<210> SEQ ID NO 6
<211> LENGTH: 12
<212> TYPE: PRT
<213> ORGANISM: Peptide from Catalase

<400> SEQUENCE: 6

Arg Leu Cys Glu Asn Ile Ala Gly His Leu Lys Asp
1               5                   10

<210> SEQ ID NO 7
<211> LENGTH: 17
<212> TYPE: PRT
<213> ORGANISM: Protein from catalase

<400> SEQUENCE: 7

Arg Leu Gly Pro Asn Tyr Leu Gln Ile Pro Val Asn Cys Pro Tyr Arg
1               5                   10                  15

Ala

<210> SEQ ID NO 8
<211> LENGTH: 10
<212> TYPE: PRT
<213> ORGANISM: Protein from lysozyme

<400> SEQUENCE: 8

Arg Cys Glu Leu Ala Ala Ala Met Lys Arg
1               5                   10

<210> SEQ ID NO 9
<211> LENGTH: 12
<212> TYPE: PRT
<213> ORGANISM: Protein from ovalbumin

<400> SEQUENCE: 9

Ala Ser Met Glu Phe Cys Phe Asp Val Phe Lys Glu
1               5                   10

<210> SEQ ID NO 10
<211> LENGTH: 12
<212> TYPE: PRT
<213> ORGANISM: Peptide from ovalbumin

<400> SEQUENCE: 10
```

Arg Ala Asp His Pro Phe Leu Phe Cys Ile Lys His
1               5                   10

<210> SEQ ID NO 11
<211> LENGTH: 14
<212> TYPE: PRT
<213> ORGANISM: Peptide from ovalbumin

<400> SEQUENCE: 11

Arg Tyr Pro Ile Leu Pro Glu Tyr Leu Gln Cys Val Lys Glu
1               5                   10

<210> SEQ ID NO 12
<211> LENGTH: 21
<212> TYPE: PRT
<213> ORGANISM: Peptide from ribonuclease

<400> SEQUENCE: 12

Lys His Ile Ile Val Ala Cys Glu Gly Asn Pro Tyr Val Pro Val His
1               5                   10                  15

Phe Asp Ala Ser Val
            20

<210> SEQ ID NO 13
<211> LENGTH: 24
<212> TYPE: PRT
<213> ORGANISM: Peptide from ribonuclease

<400> SEQUENCE: 13

Arg Cys Lys Pro Val Asn Thr Phe Val His Glu Ser Leu Ala Asp Val
1               5                   10                  15

Gln Ala Val Cys Ser Gln Lys Asn
            20

<210> SEQ ID NO 14
<211> LENGTH: 11
<212> TYPE: PRT
<213> ORGANISM: Ppetide from ribonuclease

<400> SEQUENCE: 14

Tyr Ser Thr Met Ser Ile Thr Asp Cys Arg Glu
1               5                   10

<210> SEQ ID NO 15
<211> LENGTH: 15
<212> TYPE: PRT
<213> ORGANISM: Peptide from trypsinogen

<400> SEQUENCE: 15

Lys Cys Leu Lys Ala Pro Ile Leu Ser Asp Ser Ser Cys Lys Ser
1               5                   10                  15

<210> SEQ ID NO 16
<211> LENGTH: 18
<212> TYPE: PRT
<213> ORGANISM: Peptide from trypsinogen

<400> SEQUENCE: 16

Lys Asp Ser Cys Gln Gly Asp Ser Gly Gly Pro Val Val Cys Ser Gly
1               5                   10                  15

Lys Leu